United States Patent
Li et al.

(10) Patent No.: US 8,043,815 B2
(45) Date of Patent: Oct. 25, 2011

(54) METHODS FOR ANALYSIS OF PDEF AND SURVIVIN AS INTERCONNECTED CANCER BIOMARKERS AND TARGETS FOR PERSONALIZED MEDICINE

(75) Inventors: Fengzhi Li, Buffalo, NY (US); Ali Ghadersohi, Amherst, NY (US); Pasha Apontes, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 81 days.

(21) Appl. No.: 12/186,891

(22) Filed: Aug. 6, 2008

(65) Prior Publication Data

US 2009/0081674 A1    Mar. 26, 2009

Related U.S. Application Data

(60) Provisional application No. 60/963,792, filed on Aug. 6, 2007.

(51) Int. Cl.
*C12Q 1/68* (2006.01)
(52) U.S. Cl. .................. 435/6.12; 435/91.2; 530/350
(58) Field of Classification Search ............. 435/6, 91.2; 536/23.1, 24.33
See application file for complete search history.

(56) References Cited

U.S. PATENT DOCUMENTS

| | | | |
|---|---|---|---|
| 6,692,916 | B2 * | 2/2004 | Bevilacqua et al. ............. 435/6 |
| 2004/0048254 | A1 | 3/2004 | Olek et al. |
| 2005/0026169 | A1 | 2/2005 | Cargill et al. |
| 2007/0065859 | A1 | 3/2007 | Wang et al. |
| 2008/0108081 | A1 | 5/2008 | Luke et al. |

FOREIGN PATENT DOCUMENTS

WO    2005118875 A2    12/2005

OTHER PUBLICATIONS

Ghadersohi, A. et al. Prostate derived Ets transcription factor (PDEF) downregulates survivin expression and inhibits breast cancer cell growth in vitro and xenograft tumor formation in vivo. Breast Cancer Res Treat., vol. 102, pp. 19-30, 2007, published on line Aug. 8, 2006.*
Chavez-Blanco, A. et al. Antineoplastic effects of the DNA methylation inhibitor hydralazine and the histone deacetylase inhibitor valproic acid in cancer cell lines. Cancer Cell International, vol. vol. 6, No. 2, pp. 1-9, Jan. 31, 2006.*
Ghadersohi et al. Prostate derived Ets transcription factor shows better tumor-association than other cancer associated molecules. Oncol. Rep., vol. 11(2), p. 1, abstract, 2004.*
Wu, et al.; Molecular Mechanism of Inhibition of Survivin Transcription by the GC-rich Sequence-selective DNA Binding Antitumor Agent, Hedamycin; The Journal of Biological Chemistry, Issue of Mar. 11, 2005, vol. 280, No. 10; pp. 9745-9751.
Ghadersohi, et al.; Prostate-derived Ets transcription factor (PDEF) downregulates survivin expression and inhibits breast cancer cell growth in vitro and xenograft tumor formation in vivo; Breast Cancer Res Treat (2007), vol. 102; pp. 19-30.
ISSA; DNA Methylation as a Therapeutic Target in Cancer; Clin Cancer Res., Mar. 15, 2007, vol. 13, No. 6; pp. 1634-1637.
Shah et al.; Selenium disrupts estogen receptor a signaling and potentiates tamoxifen antagonism in endometrial cancer cells and tamoxifen-resistant breast cancer cells; Mol Cancer Ther, Aug. 2005, vol. 4, No. 8; pp. 1239-1249; Abstract.
Ghadersohi et al.; Prostate derived Ets transcription factor shows better tumor-association than other cancer-associated molecules; Oncol Rep., Feb. 2004, vol. 11, No. 2; 1 page; Abstract.
Feldman et al.; Pdef Expression in Human Breast Cancer Is Correlated with Invasive Potential and Altered Gene Expression; Cancer Research, Aug. 2003, vol. 63, No. 15; pp. 4626-4631; Abstract.

* cited by examiner

*Primary Examiner* — Prabha Chunduru
(74) *Attorney, Agent, or Firm* — Hodgson Russ LLP

(57) ABSTRACT

Provided are methods for determining whether an individual is a candidate to receive treatment with a DNA methylation inhibitor. The method can be performed a biological sample of cancerous tissue of the individual. Determining that PDEF expression is absent or low and survivin expression is present identifies the individual as a candidate to receive a treatment with a DNA methylation inhibitor. The method also includes communicating the result of identifying an individual as a candidate for receiving a DNA methylation inhibitor to a health care provider.

8 Claims, 11 Drawing Sheets

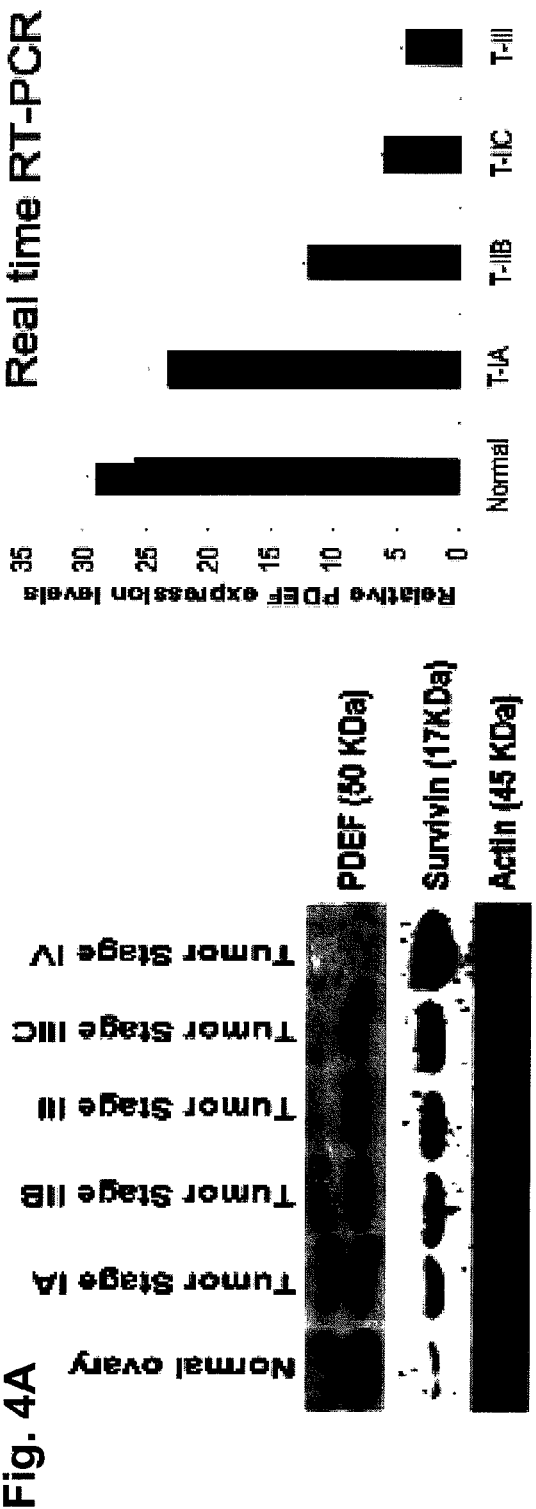

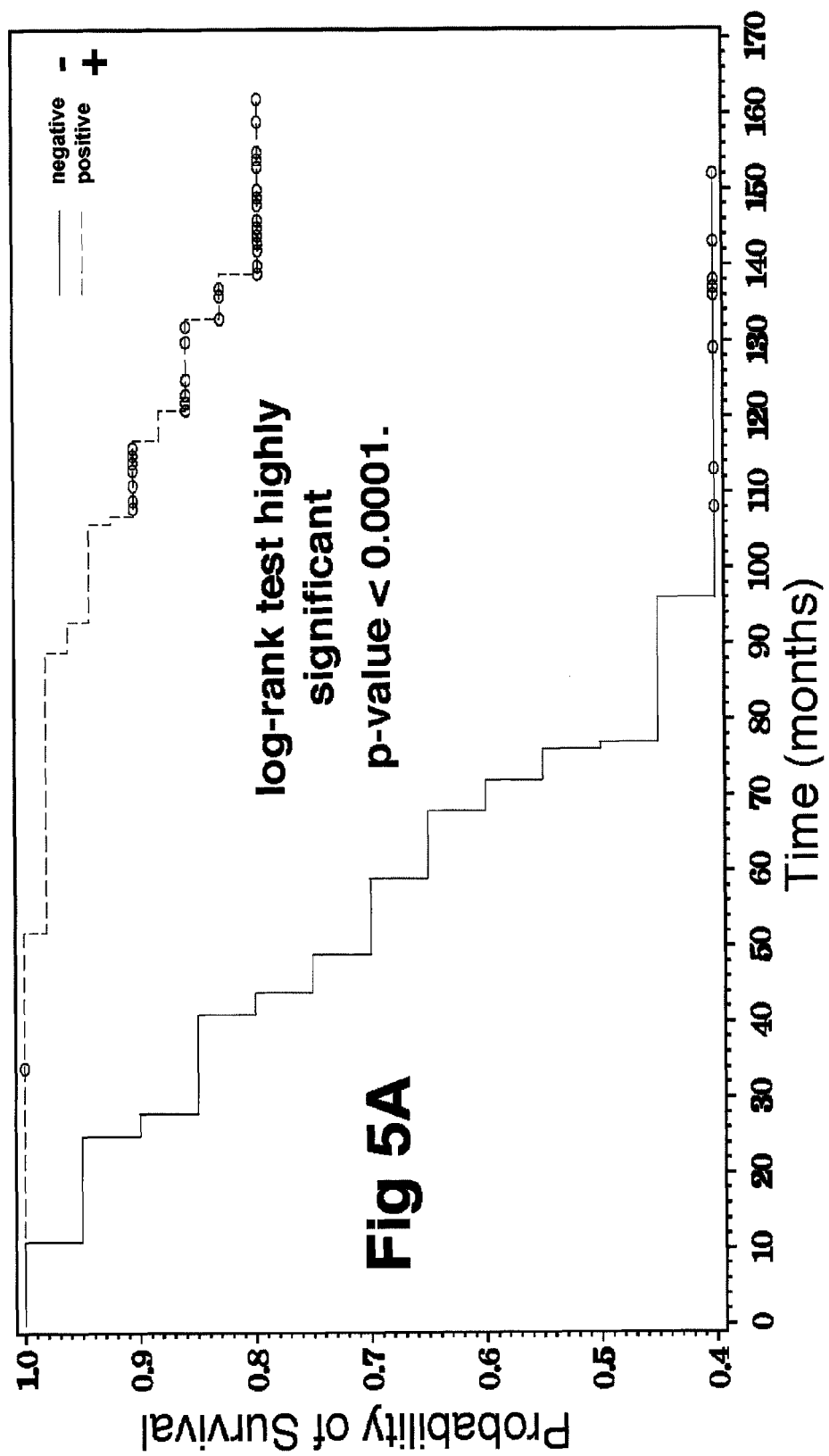

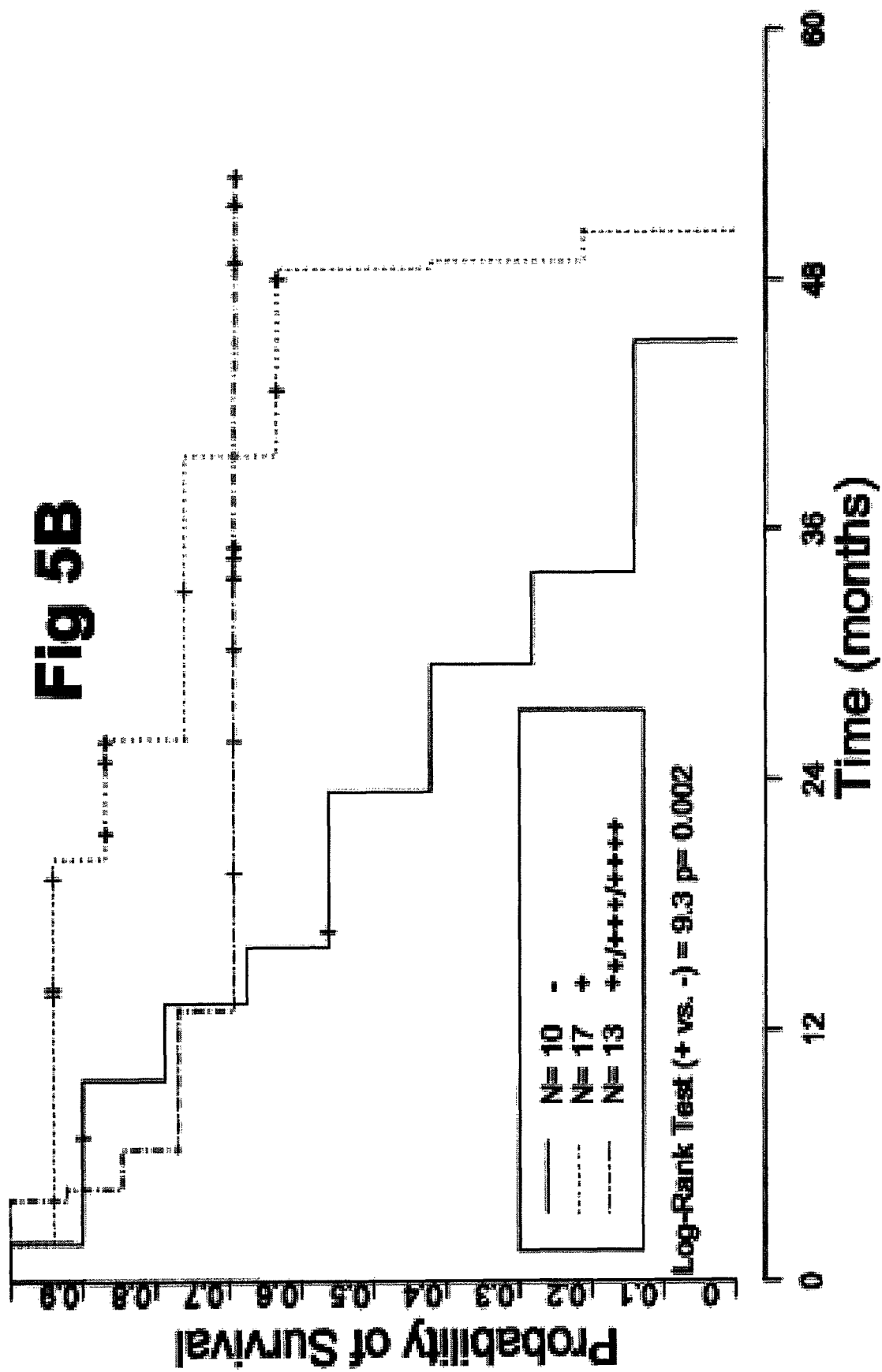

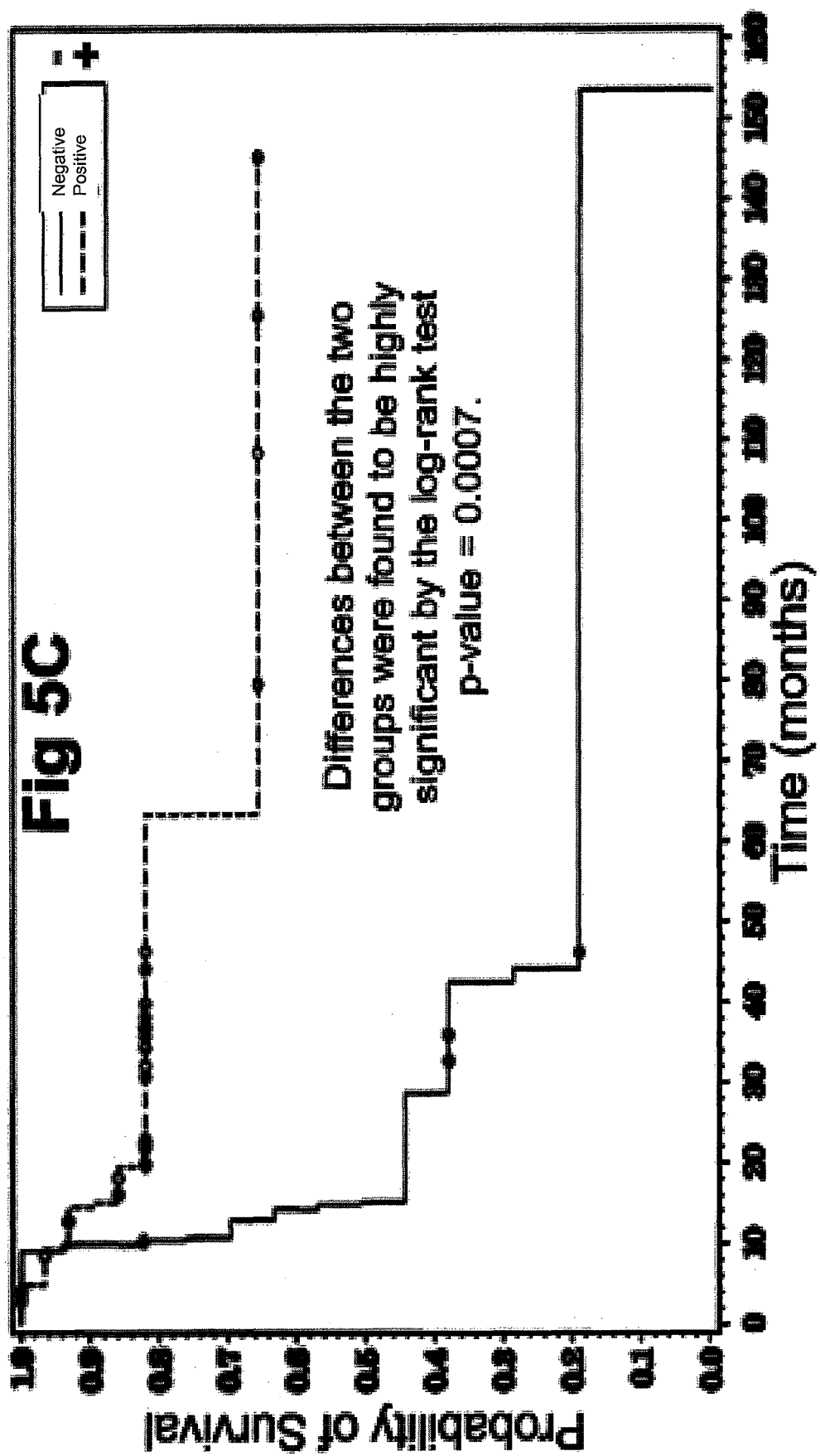

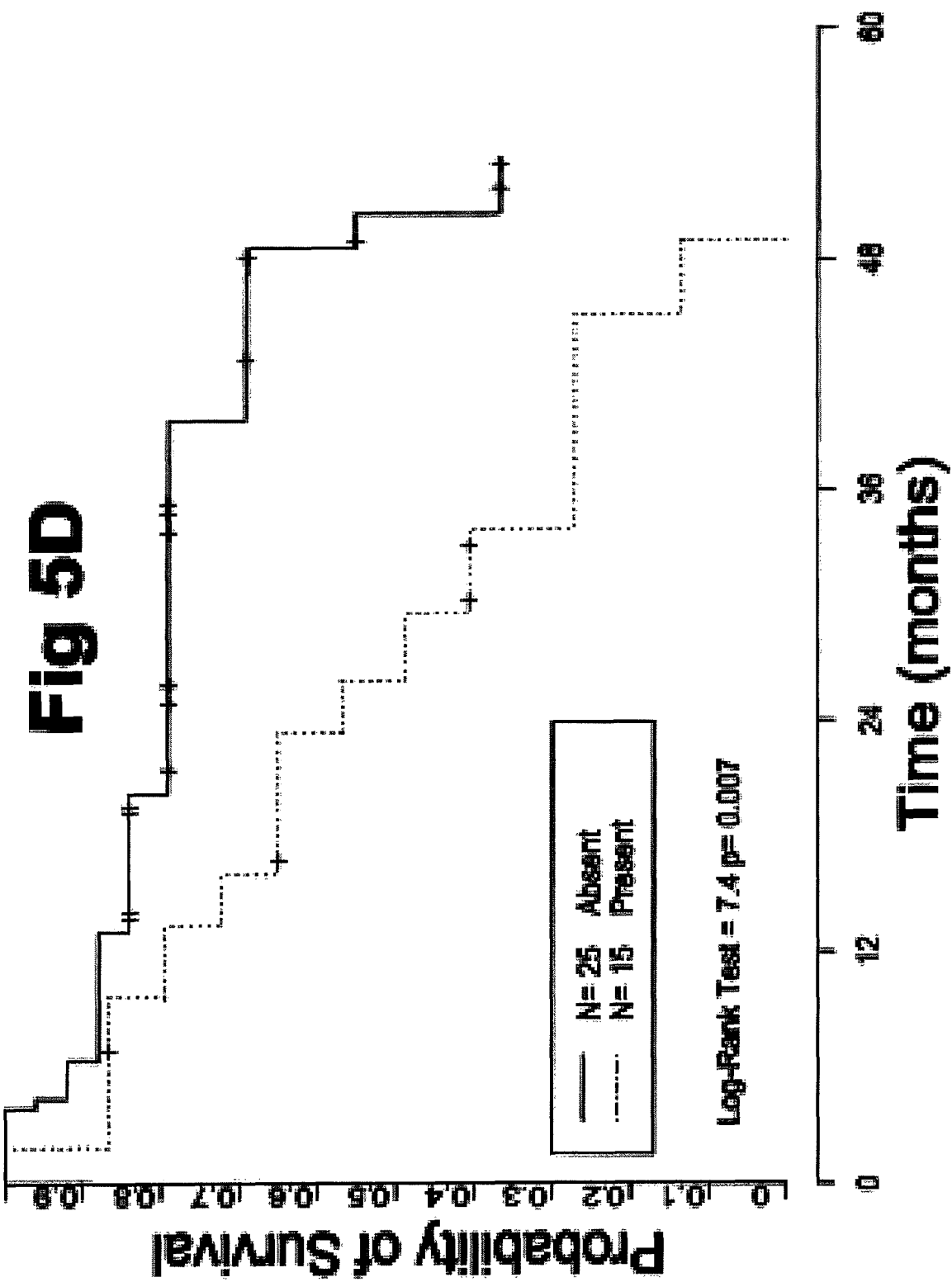

METHODS FOR ANALYSIS OF PDEF AND SURVIVIN AS INTERCONNECTED CANCER BIOMARKERS AND TARGETS FOR PERSONALIZED MEDICINE

This application claims priority to U.S. application Ser. No. 60/963,792, filed on Aug. 6, 2007, the entire disclosure of which is incorporated herein by reference.

FIELD OF THE INVENTION

This invention relates generally to the field of cancer and more specifically to tools and methods for identifying cancer patients and candidates for personalized treatments.

DESCRIPTION OF RELATED ART

Certain cancer biomarkers, such as the apoptosis inhibitor survivin, are known to be associated with malignancy. For example, survivin is highly expressed in all common cancers, but is generally undetectable in differentiated, post-mitotic normal tissues (Altieri, D. C. Nat Rev Cancer, 3: 46-54, 2003; Li, F. J Cell Physiol, 197: 8-29, 2003; Li, F. and Ling, X. J Cell Physiol, 208: 476-486, 2006). Survivin also appears to play an essential role in progression of many types of malignancies. However, the reasons for this differential expression of survivin in normal verses malignant tissues have not been fully elucidated. Further, while survivin expression appears to be inversely correlated with expression of prostate-derived Ets transcription factor (PDEF) (Ghadersohi et al., (2007) Breast Cancer Res Treat Vol. 102, pp 19-30), it is not known how or why PDEF protein becomes apparently downregulated in malignant tissues. Therefore, there is an ongoing need to further develop biomarkers associated with cancer for use in identification of cancer patients as candidates for individualized therapies based on their expression patterns of such biomarkers.

SUMMARY OF THE INVENTION

The present invention provides a method for determining whether an individual diagnosed with cancer is a candidate for treatment with a DNA methylation inhibitor. The method comprises obtaining a biological sample of cancerous tissue from the individual and determining the expression of PDEF and survivin from the sample. A determination that PDEF expression is absent or low relative to a control and that the sample is positive for survivin expression indicates that the individual is a candidate for receiving a DNA methylation inhibitor. A determination that PDEF expression is normal or high and survivin expression is absent indicates that the individual is a not a candidate for receiving the DNA methylation inhibitor. A determination that PDEF expression is absent or low and that survivin expression is absent is also indicative that the individual is a not a candidate for receiving the DNA methylation inhibitor. Determining that PDEF expression is normal or high and detecting survivin expression is likewise indicative that the individual is a not a candidate for receiving the DNA methylation inhibitor. Identification of an individual as a candidate for receiving a DNA methylation inhibitor is considered to also be indicative that the individual is a candidate for receiving a histone deacetylase inhibitor in combination with the DNA methylation inhibitor. The invention includes communicating the result of identifying an individual as a candidate for receiving a DNA methylation inhibitor to a health care provider.

BRIEF DESCRIPTION OF THE DRAWINGS

FIG. 4A provides a photographic representation of detection of the association of loss of PDEF expression with upregulation of survivin that occurs in ovarian tumor grades. FIG. 4B provides a graphical representation of results obtained from detection of PDEF mRNA in progressive grades of ovarian cancer tissues by Real time RT-PCR. FIG. 4C provides a tabular summary of results from detecting PDEF and survivin protein expression. Similar results were obtained in breast, prostate and lung cancers.

FIGS. 5A, 5B and 5C provide graphical representations of results showing that loss of PDEF expression is strongly associated with poor survival for patients with prostate (FIG. 5A), ovarian (FIG. 5B) or lung (FIG. 5C) cancer, shown as Log-Rank tests of patient survival curves. FIG. 5D provides a graphical example of results showing that loss of survivin expression in ovarian cancer is strongly associated with favorable survival for cancer patients, shown as Log-Rank tests of patient survival curves.

DETAILED DESCRIPTION OF THE INVENTION

Figure 1:
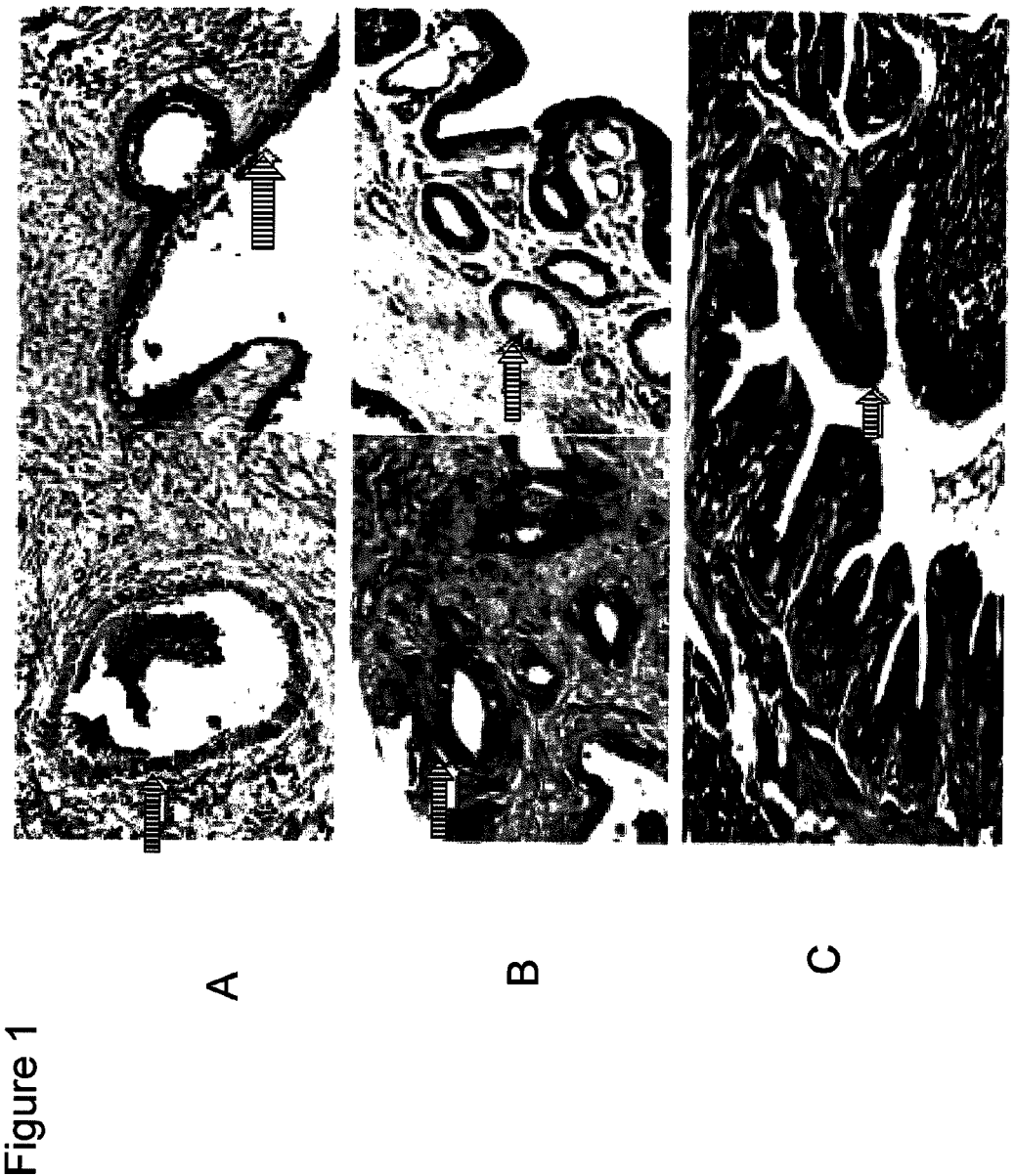
FIG. 1 provides a photographic representation of immunohistochemistry detection of highly PDEF expression in human normal ovarian (panel A), prostate (panel B) and lung (panel C) determined by immunohistochemistry (IHC). Corresponding normal IgG controls were negative (not shown). Hatched arrows indicate epithelial cell layers.

The present invention provides methods for identifying whether or not an individual diagnosed with cancer is a candidate for receiving a DNA methylation inhibitor. The method comprises obtaining a biological sample of cancerous tissue from the individual and determining PDEF expression and survivin expression from the sample. Determining that PDEF expression is absent or low and that the sample is positive for survivin expression is indicative that the individual is a candidate for receiving the DNA methylation inhibitor. Conversely, determining that PDEF expression is normal or high and survivin expression is absent is indicative that the individual is a not a candidate for receiving the DNA methylation inhibitor. Likewise, determining that PDEF expression is absent or low and that survivin expression is absent is indicative that the individual is a not a candidate for receiving the DNA methylation inhibitor. Determining that PDEF expression is normal or high and detecting that survivin is highly expressed is also indicative that the individual is a not a candidate for receiving the DNA methylation inhibitor.

Determining that PDEF or survivin expression is absent in the method of the invention means that PDEF or survivin is undetectable in the particular assay employed in the determination of expression.

Determining that PDEF expression is low is considered to mean that less PDEF expression is detected from the cancer sample than from a control. Determining that PDEF expression is high is considered to mean that more PDEF is detected from the cancer sample than that detected from a control.

The control may be any suitable control. Some non-limiting examples include a sample of non-cancerous tissue (or non-cancerous blood or lymph) obtained from the same individual being tested in the method of the invention. Such a control is preferably obtained from the same organ or tissue type from which the sample of cancerous tissue is obtained. Alternatively, the control may be a sample obtained from a different individual, such as a person matched with the individual being tested for particular characteristics, examples of which characteristics include but are not limited to age, gender, weight, occupation, status as a tobacco user, and combinations thereof (i.e., the person providing the control sample is considered a matched control).

As another alternative, the control can be a standardized curve generated from data obtained from any method(s) of analyzing PDEF expression. Such a control may be stored electronically and used for comparison to the experimental results via, for example, a computer program.

It will be recognized that survivin is generally considered to be absent from normal (non-cancerous) cells. Nevertheless, any suitable control for survivin expression may also be used in the method of the invention to control for rare circumstances wherein survivin expression could be detected from samples of non-cancerous tissues, and/or to control for background signal.

The biological sample obtained from the individual can be any biological sample that contains cancerous cells, including but not limited to tumor biopsies and samples of blood or lymph. In the case of an individual diagnosed with bladder cancer cancer, the biological sample can be urine that is expected to contain prostate cancer cells.

DNA methylation inhibitors and methods for treating cancer with DNA methylation inhibitors, as well as for treating an individual with a DNA methylation inhibitor in combination with other agents, such as a histone deacetylase inhibitor, are known in the art. Some examples are provided in U.S. Pat. No. 7,276,228 and U.S. Patent Publication Nos. 20080175814 and 20070105792. The descriptions of methylation inhibitors, histone deacetylase inhibitors, and methods of using such agents for treating cancer in an individual are incorporated herein by reference. Identification of an individual as a candidate for receiving a DNA methylation inhibitor is also considered to be an indicative that the individual is a candidate for receiving a histone deacetylase inhibitor in combination with the DNA methylation inhibitor. In one embodiment, the histone deacetylase inhibitor may be Trichostatin A (TSA).

As will be recognized in the art, the major enzyme responsible for maintenance of DNA methylation patterns during replication is the DNA methyltransferase known as DNMT1. Thus, while the method of the invention may be employed to identify an individual as a candidate for receiving an agent that inhibits methylation by inhibiting any DNA methyltransferase expressed in the individual, in one embodiment, the inhibited DNA methyltransferase is DNMT1.

In particular embodiments, an individual identified by the method of the invention may be a candidate for receiving a DNA methylation inhibitor that is a cytidine analog or derivative thereof. Examples of cytidine analogs or derivatives include but are not limited to 5-azacytidine and 5-aza-2'-deoxycytidine (decitabine). In another embodiment, the DNA methylation inhibitor may be a quinoline derivative.

Notwithstanding progress in using DNA methylation inhibitors for therapeutic purposes, determining which individuals would be particularly likely to benefit from DNA methylation inhibitor treatment has been problematic, and may explain why it has been difficult to interpret results from some clinical trials designed to analyze the effects of candidate DNA methylation inhibitors for treating various neoplastic conditions. The present invention addresses this problem in the context of identifying cancer patients as candidates for receiving a DNA methylation inhibitor by analyzing PDEF and survivin expression in tumor samples.

In particular, we have discovered that the PDEF gene is hypermethylated in malignant cells. Hypermethylation is considered to be present when a majority or all of cytosine residues in the CpG motif of a particular CpG island are methylated. We have determined that hypermethylation of the PDEF gene results in absent or reduced expression of PDEF, which in turn results in increased expression of survivin. This is of importance because survivin expression directly correlates with cancer stage, drug/radiation resistance and shorter patient survival (Li, F. J Cell Physiol, 197: 8-29, 2003; Li, F. and Ling, X. J Cell Physiol, 208: 476-486, 2006; Altieri, D. C. Adv Cancer Res, 88: 31-52, 2003; Li, F. Br J Cancer, 92: 212-216, 2005) as well as oncogenesis, especially in virus-induced carcinogenesis and colorectal tumorigenesis (Ling, X. J Cell Physiol, 208: 476-486, 2006; Br J Cancer, 92: 212-216, 2005), while PDEF has been shown to act as a tumor suppressor and a metastasis inhibitor (Gu, X., et al. Cancer Res, 67: 4219-4226, 2007). Therefore, the method of the invention is useful for identifying individuals as candidates for receiving a DNA methylation inhibitor, since it is expected that administration of a DNA methylation inhibitor to an individual with cancer will inhibit maintenance of methylation of the PDEF gene, which will result in a concomitant reduction in survivin expression, thereby providing a therapeutic effect to the individual. In connection with this, we demonstrate that treatment of PDEF negative cancer cells with a methylation inhibitor restores PDEF expression, and that restoration of PDEF expression reduces the expression of survivin.

The present invention is expected to be of benefit in not only identifying individuals who may benefit from treatment with a DNA methylation inhibitor, but also in identifying individuals who are expected to be less likely to benefit from such treatment. The method of the invention is therefore expected to be useful not only for providing individualized treatment recommendations for cancer patients, but also in selecting participants for clinical trials wherein the efficacy of a candidate DNA methylation inhibitor is evaluated. Accordingly, the method of the invention can further comprise communicating the results of determining whether or not an individual is a candidate for receiving a DNA methylation inhibitor to a health care provider. Thus, the results may be considered a product of the method of the invention. The results may be communicated by any means, such as electronically or telephonically.

The health care provider to whom the results are communicated may be any individual involved in diagnosis, treatment, or development of treatment protocols for cancer patients. Examples of such health care providers include but are not limited to physicians, physician's assistants, pharmacists, nurses, and entities such as pharmaceutical companies, and individuals involved in recruitment, screening and/or selection of subjects for a clinical trial of a DNA methylation inhibitor, either alone or in combination with other agents or therapeutic interventions.

Thus, it will be apparent that an individual identified as having normal or high PDEF expression would not be considered a candidate for treatment with a methylation inhibitor. It could accordingly be decided not to administer a methylation inhibitor to such an individual in a clinical treatment setting, or to not include such an individual in a clinical trial of a candidate DNA methylation inhibitor. Conversely, determining low or absent PDEF expression in a biological sample of cancerous tissue obtained from an individual is considered to be indicative that the PDEF gene in the sample is likely methylated. Therefore, when PDEF expression is absent or low, and when survivin is also detected in the sample, the individual is considered to be a candidate to receive a DNA methylation inhibitor, and the individual could be prescribed a DNA methylation inhibitor by a health care professional, or be selected for inclusion in a clinical trial of a candidate DNA methylation inhibitor.

In the present invention, PDEF and survivin expression can be determined by any suitable method, such as by any conventional nucleic acid detection or protein immunodetection method for detecting PDEF or survivin mRNA or protein. The DNA sequences encoding human PDEF and survivin mRNA and protein are well known in the art. Also recognized are variations in transcription of the PDEF gene, such as PDEF transcripts that are initiated within the second exon of the PDEF gene.

For protein detection, immuno-detection methods may be used. Antibodies reactive with PDEF and antibodies reactive with survivin are known in the art and are commercially available. In general, immuno-detection can be performed by immunohistochemistry or by detecting proteins purified from particular biological samples. Non-limiting examples of methods suitable for immuno-detection of PDEF or survivin protein include Western blotting and ELISA assays.

In one embodiment, ELISA assays can be performed with secondary IgG conjugated to, for example, a detectable label, such as Horseradish peroxidase or alkaline phosphatase (colorimetric ELISA). Alternatively, ELISA assays can be performed with an antibody that is directly conjugated to a colorimetric. In another alternative, the expression of PDEF and survivin may be determined by fluorescence dye (such as FITC, Alexa-Fluor or Qdot)-labeled secondary antibody in ELISA assays (fluorometric ELISA). Both colorimetric and fluorometric ELISA can also be performed using a variety of suitable modifications, such as by using biotinylated-anti-PDEF or anti-survivin antibodies, followed by applying streptavidin conjugated to a colorimetric enzyme such as Horseradish peroxidase or to a fluorescent agent such as FITC. The biotin-streptavidin approach can also be performed by using a biotinylated anti-IgG secondary antibody instead of directly conjugating biotin to anti-PDEF or anti-survivin antibodies.

In another embodiment, the expression of PDEF and survivin in tumor tissue samples or urine (i.e., for bladder cancer) may be determined by conventional Western blots performed according to well known techniques. Generally, Western blot analysis of PDEF may use 10% SDS-polyacrylamide gel electrophoresis (SDS-PAGE) gels, while Western blot analysis of survivin may use 15% SDS-PAGE gels. Western blot-specific nitrocellulose membranes in 0.45 µm are suitable for PDEF analysis, while 0.2 µm for survivin may be employed. Signals from the Western blots may be detected using regular or high sensitive ECL protein detection kits and visualized by autoradiography with X-ray film. Alternatively, colorimetric or fluorometric techniques may be used.

In another embodiment, the expression of PDEF and survivin protein in tumor tissue samples may be determined by immunohistochemistry using conventional techniques, including by using fluorescence-labeled primary antibodies against PDEF or survivin.

In another embodiment, the expression of survivin or PDEF can be determined by detecting the presence of their respective mRNA transcripts using any suitable mRNA detection method. Some non-limiting examples include semi-quantitative RT-PCR (qRT-PCR) or real-time qRT-PCR.

In the method of the invention, determining that PDEF expression is absent or low relative to a control is considered to be evidence that the PDEF gene is methylated such that transcription of the PDEF gene (and thus translation of the PDEF protein) is inhibited. It will be recognized by those skilled in the art that a determination of PDEF expression that is absent or low relative to a control can be related to methylation status of the PDEF gene if desired by more direct analysis of the methylation status of the PDEF gene using any suitable method. Some non-limiting examples of suitable methods for analyzing DNA methylation include bisulfite treatment of DNA, reverse phase high pressure liquid chromatography (HPLC), methylation sensitive PCR (MSP), Bisulfite PCR, cloning differentially methylated sequences, Southern blot analysis, Methylated CpG island amplification (MCA), differential methylation hybridization using CpG island arrays, isolation of CpG islands using a CpG binding column, DNA-methyltransferase assay, bisulfite modification, methylation detection after restriction, methylation-sensitive restriction fingerprinting, restriction landmark genomic scanning (RLGS), and bisulfite conversion combined with bisulfite restriction analysis (COBRA).

In one embodiment, bisulfite treatment is used. The bisulfate method is used to convert unmethylated cytosines to uracil. The bisulfite treated DNA may be amplified and sequenced to determine the methylation status of CpG sites, where uracil is read as thymine (T) in the sequence of the amplified DNA when methylation is not present. However, since methylated cytosines are not converted to uracil by bisulfite treatment, they are read as cytosine (C), when analyzing methylated DNA.

Thus, it will be apparent to those skilled in the art that determining whether an individual is a candidate for receiving a DNA methylation inhibitor can be performed according to the method of the invention using any suitable method for determining PDEF and survivin expression.

The invention is further illustrated by the following Figures and description, which are not intended to be limiting.

EXAMPLE 1

This Example demonstrates expression of PDEF in epithelial cell layers of various human normal tissues, that PDEF expression is reduced in early stage or non-metastatic tumors and is absent in later stage or metastatic tumors, that loss of PDEF expression is associated with upregulation of survivin in ovarian, breast, prostate and lung cancer tissues and cell lines.

We have demonstrated that PDEF protein is highly expressed in epithelial cells of human normal mammary glands. As shown in FIG. 1, PDEF is also highly expressed in epithelial cells of human ovarian (panel A), prostate (panel B) and lung (panel C) determined by immunohistochemistry (IHC). Corresponding normal IgG controls were negative (not shown). Hatched arrows indicate epithelial cell layers.

Figure 2:
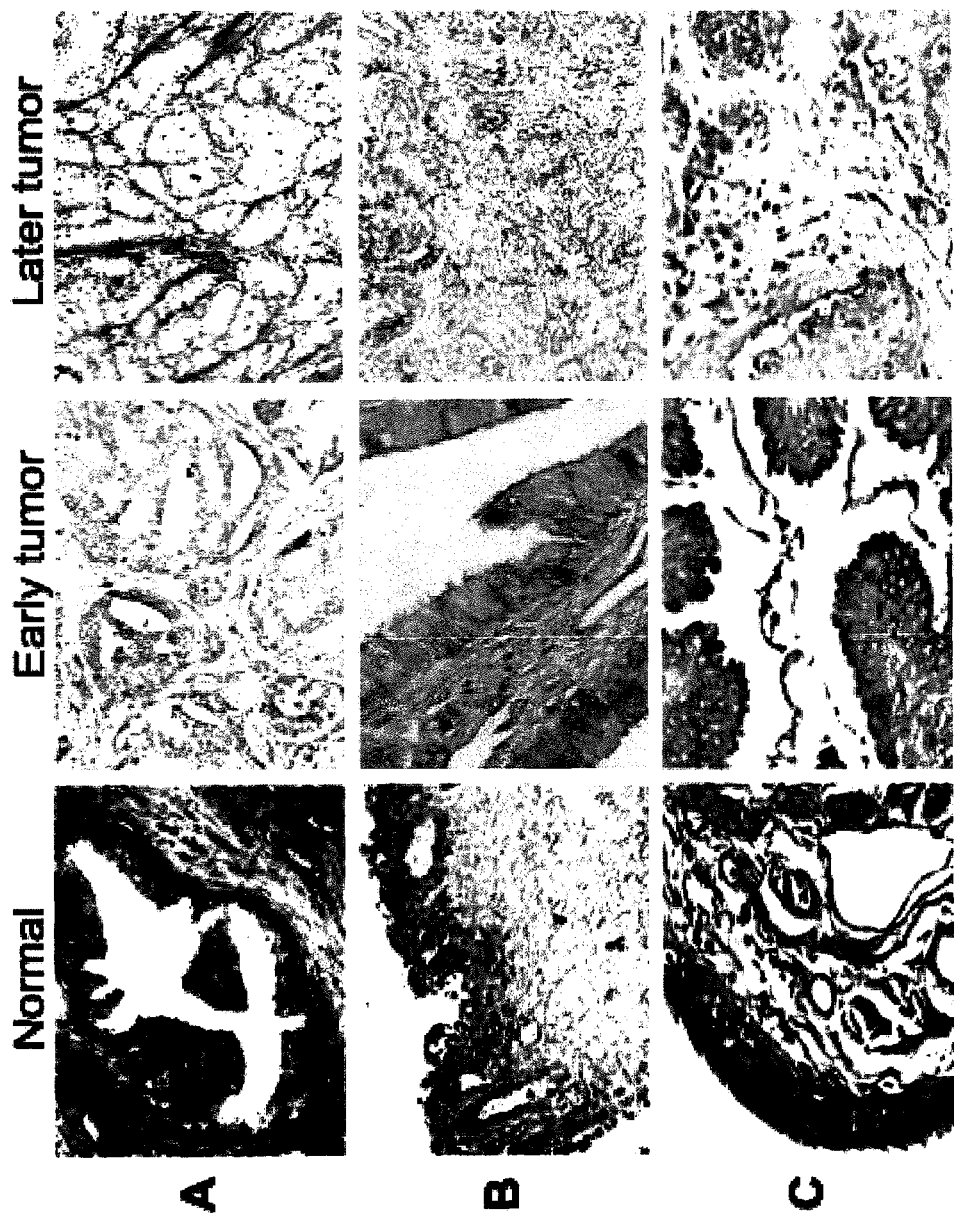
FIG. 2 provides a photographic representation of immunohistochemistry detection of reduction of PDEF expression from early stage or non-metastatic tumors to later stage or metastatic tumors for prostate (panel A), ovarian panel B) and lung (panel C) cancer tissues.

As shown in FIG. 2, PDEF expression is reduced in early stage or non-metastatic tumors, and is not detected in later stage or metastatic tumors. In particular, in addition to reduced or absent PDEF expression in breast cancer, PDEF expression exhibits this pattern in prostate (panel A), ovarian (panel B) and lung (panel C) cancer tissues.

Figure 3:
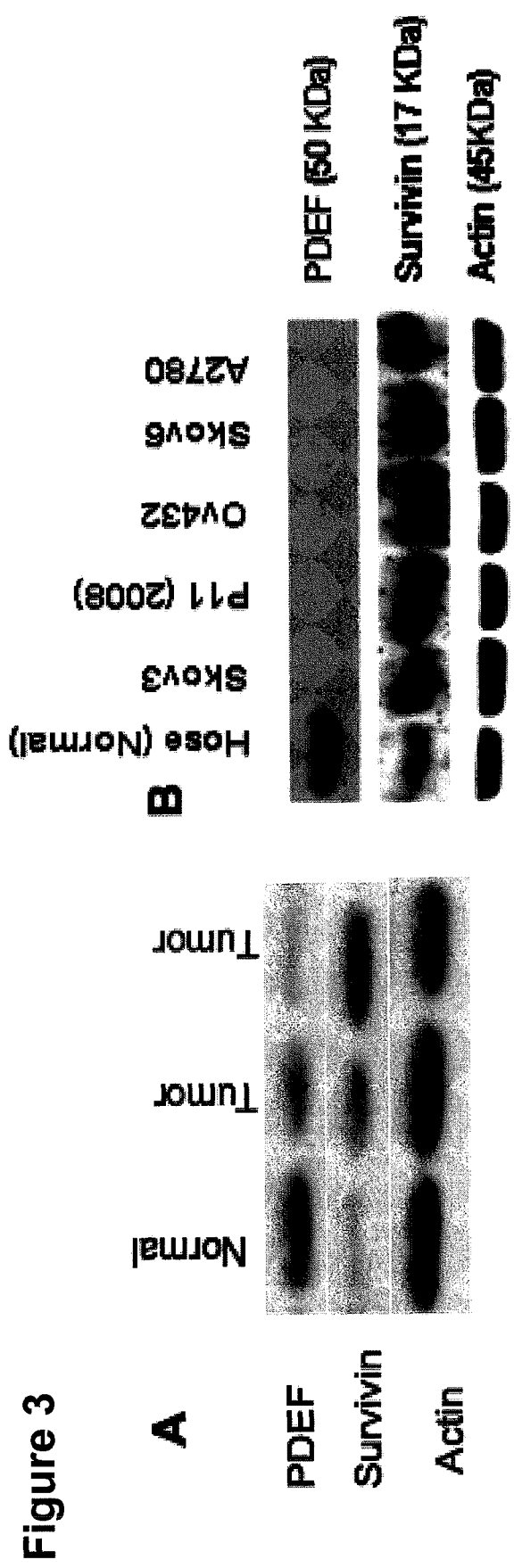
FIG. 3 provides a photographic representation of detection of the association of loss of PDEF expression with upregulation of survivin in both ovarian cancer tissues (panel A) and ovarian tumor cell lines (panel B). Similar results were obtained in breast, prostate and lung cancer tissues and cell lines.

As shown in Western blotting experiments, the results of which are depicted in FIG. 3, loss of PDEF expression is associated with upregulation of survivin in both ovarian cancer tissues (panel A) and ovarian tumor cell lines (panel B). Similar results were obtained in breast, prostate and lung cancer tissues and cell lines.

As shown in FIGS. 4A, 4B and 4C, expression of PDEF and survivin is inversely associated with ovarian tumor grades. Results from detection of PDEF protein is shown in FIGS. 4A and 4C; PDEF mRNA detection is summarized in FIG. 4 B). As can be seen from these figures, during ovarian cancer progression from early stage to high tumor grade the expression of PDEF is reduced, while the expression of survivin shows the opposite pattern (FIGS. 4A and 4C). Similar results were obtained in breast, prostate and lung cancers.

EXAMPLE 2

This Example demonstrates that expression of PDEF in cancer tissues is associated with significantly longer cancer patient survival. Consistent with our findings shown in FIGS. 3 and 4, an analysis of a cohort of clinical specimens indicates that loss of PDEF expression is strongly associated with poor survival for patients with prostate (FIG. 5A), ovarian (FIG. 5B) or lung (FIG. 5C) cancer, shown as Log-Rank tests of patient survival curves. PDEF-positive versus PDEF-negative tumors shows a significant difference in the survival probability for the two distinct patient groups (p value $\ll 0.05$). In contrast, expression of survivin in tumor tissues is associated with a worse survival for cancer patients shown as an example for ovarian cancer (FIG. 5D). The data presented in FIG. 5A are also summarized in Table 1.

TABLE 1

| Group | Sample size | Median survival (mo) | 2 year survival | 3 year survival | 8 year survival |
|---|---|---|---|---|---|
| PDEF Negative | 20 | 76.5 | 95% | 85% | 40% |
| PDEF Positive | 53 | Not reached | 100% | 100% | 94% |

The data presented in FIG. 5C are also summarized in Table 2.

TABLE 2

| Group | Sample size | Median survival (mo) | 1 year survival | 2 year survival | 3 year survival |
|---|---|---|---|---|---|
| PDEF Negative | 18 | 15.2 | 69.7% | 44.3% | 38.0% |
| PDEF Positive | 31 | Not reached | 93.2% | 82.1% | 82.1% |

EXAMPLE 3

This Example describes our discovery of a CpG island in the PDEF gene at the alternative promoter (Intron 1)/alternative exon 1 (exon 2) junction region, and determining methylation of that region in cancerous tissue samples. It is believed methylation in this region is responsible for the decreased PDEF expression in cancer tissues, which results in increased survivin expression, as well as poor outcomes for patients who exhibit this expression pattern.

We analyzed of the entire PDEF gene using the Pyro Q-CpG Software from Biotage (Uppsala, Sweden) and MethPrimer available at (www.urogene.org/methprimer/indexl.html) and discovered several CpG Islands across the gene. We experimentally analyzed the CpG Island at the alternative promoter (Intron 1)/alternative exon 1 (exon 2) junction region. The sequence of this CpG island is presented as SEQ ID NO: 1. Additional CpG islands are presented in SEQ ID NOs:2, SEQ ID NO:3, SEQ ID NO:4 and SEQ ID NO:5 and may also be methylated when PDEF expression is low or absent in cancer tissues.

To ascertain the methylation status of CpG motifs in PDEF-negative tumor cells and tissues, genomic DNA was isolated from PDEF-negative cancer cells and tumor tissues of breast, prostate, ovarian and lung. After the isolated DNA was treated with sodium bisulfite, the PDEF gene CpG Island (exon 1 region) of interest was PCR-amplified with the primer pair of pdef-E1f (TTAGGTAGTTAATAGATATA; SEQ ID NO:6) and pdef-E1r (biotin-AATAAACTAAAACTC-CAATCCC; SEQ ID NO:7) using bisulfite-treated DNA as templates. The resultant PCR products (187 bp) were purified and then pyrosequenced with an internal primer pyro-E1 (GTCGTTAGTTTAAATAGTAG; SEQ ID NO:8), and the pyrosequencing data (not shown) were further verified using conventional cycle sequencing with four-color fluorescently labeled dideoxy terminators.

DNA sequences derived from a total of 10 PCR products of cancer cell lines (2), ovarian cancer tissues (3), breast cancer tissues (3) and prostate cancer tissues (2) are identical and showed hypermethylation in the PDEF gene CpG island exon 1 region presented in SEQ ID NO: 1. All "C" in the CpG motifs were determined to be methylated, while all "C" outside of CpG motifs were determined to be without methylation.

Together, these data strongly support that hypermethylation of the PDEF gene CpG island in PDEF-negative cancer cells and tumor tissues is involved in PDEF silencing, and that demethylation of the CpG Island in the PDEF gene could restore the expression of PDEF and downregulates survivin.

We also analyzed the methylation status of a survivin gene CpG Island in survivin-positive tumor cells and tissues. Selected survivin-positive cells and tissues were used to isolate genomic DNA. After the isolated DNA was treated with sodium bisulfite, the DNA fragment containing the survivin gene CpG Island was PCR-amplified with the primer pair of surv-F1 (TGG TTA GGT TGG TTT TGA ATT T; SEQ ID NO:9) and surv-R3 (AAA ACC CAA CCA CAA TAA CCT C; SEQ ID NO:10) using bisulfite-treated DNA as templates. A 1/500 resultant PCR products (619 bp) was then used as PCR templates for a nest PCR amplification with the primer pair of surv-F4 (TGG TTT TGA ATT TTA GGA TTT AAG TG; SEQ ID NO:11, internal nest primer) and surv-R3 to obtain the specific nest PCR product (610 bp), which was then purified by passing through a small PCR product purification column. The purified PCR product (610 bp) was directly used for regular cycle sequencing using the surv-R3 primer without further subcloning. The results showed that all "C", regardless of being present inside or outside of CpG motifs were converted to "T" (the reverse primer surv-R3 was used for sequencing). Thus, despite the presence of CpG islands in the survivin gene, no methylation was identified in the tumor tissues.

EXAMPLE 4

This Example demonstrates restoration of PDEF expression in PDEF-negative cancer cells by treatment with methylation inhibitor.

Figure 6A:
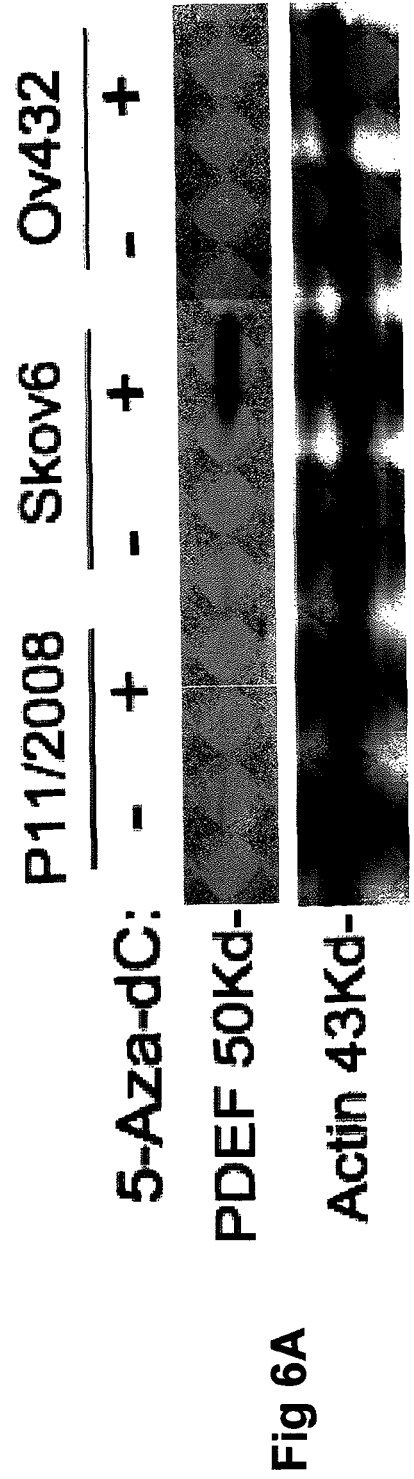
FIGS. 6A and 6B provide photographic representations of results obtained from Western blotting analysis of PDEF expression in PDEF-negative ovarian cancer cell lines treated with and without 5-aza-2-deoxycytidine (5-Aza-dC) for 5 days at 1 µM (FIG. 6A) or different concentrations of 5-Aza-dC (FIG. 6B). Two of the four ovarian cancer cell lines show restored expression of PDEF (FIGS. 6A and 6B) which also show that restoration of PDEF expression reduces or eliminates the expression of survivin (FIG. 6B).
Figure 6B:
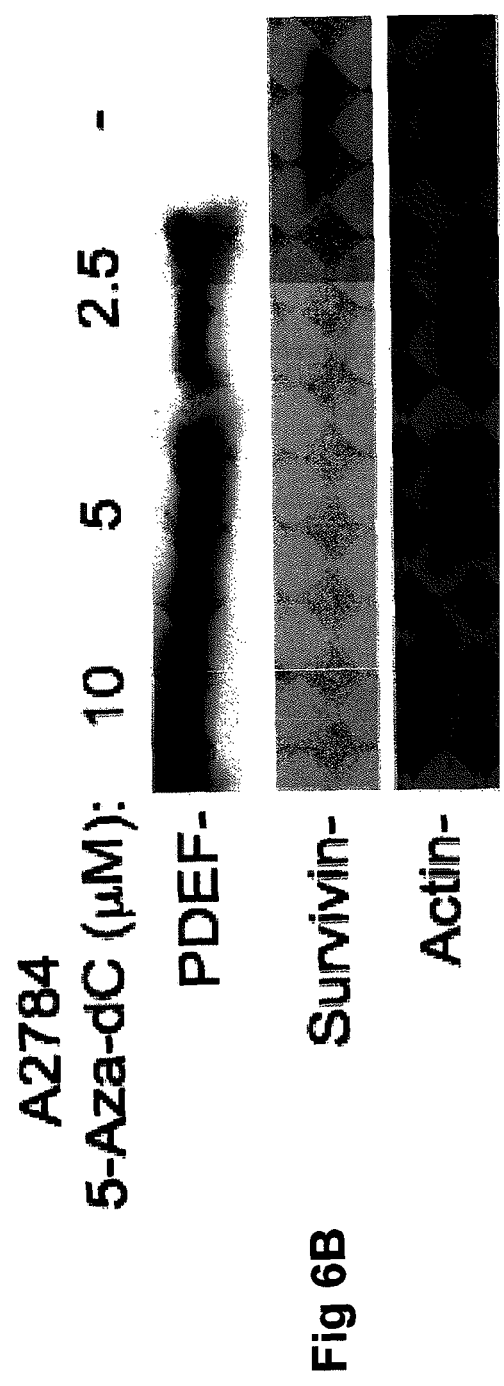

We analyzed whether the loss of PDEF expression in cancer tissues during cancer progression is the result of epigenetic methylation of the PDEF gene. Four PDEF-negative ovarian cancer cell lines were treated with and without the methylation inhibitor 5-aza-2-deoxycytidine (5-Aza-dC) for 5 days at 1 µM (FIG. 6A) or different concentration of 5-Aza-dC (FIG. 6B). Cells were then lysed and analyzed for PDEF expression by Western blots. The results revealed that two of the four ovarian cancer cell lines showed restored expression of PDEF (FIGS. 6A and 6B). This finding indicates that epigenetic methylation of the PDEF gene occurs at least in some ovarian cancer cell lines. Importantly, restoration of PDEF expression reduces or eliminates the expression of survivin (middle panel).

Figure 7:
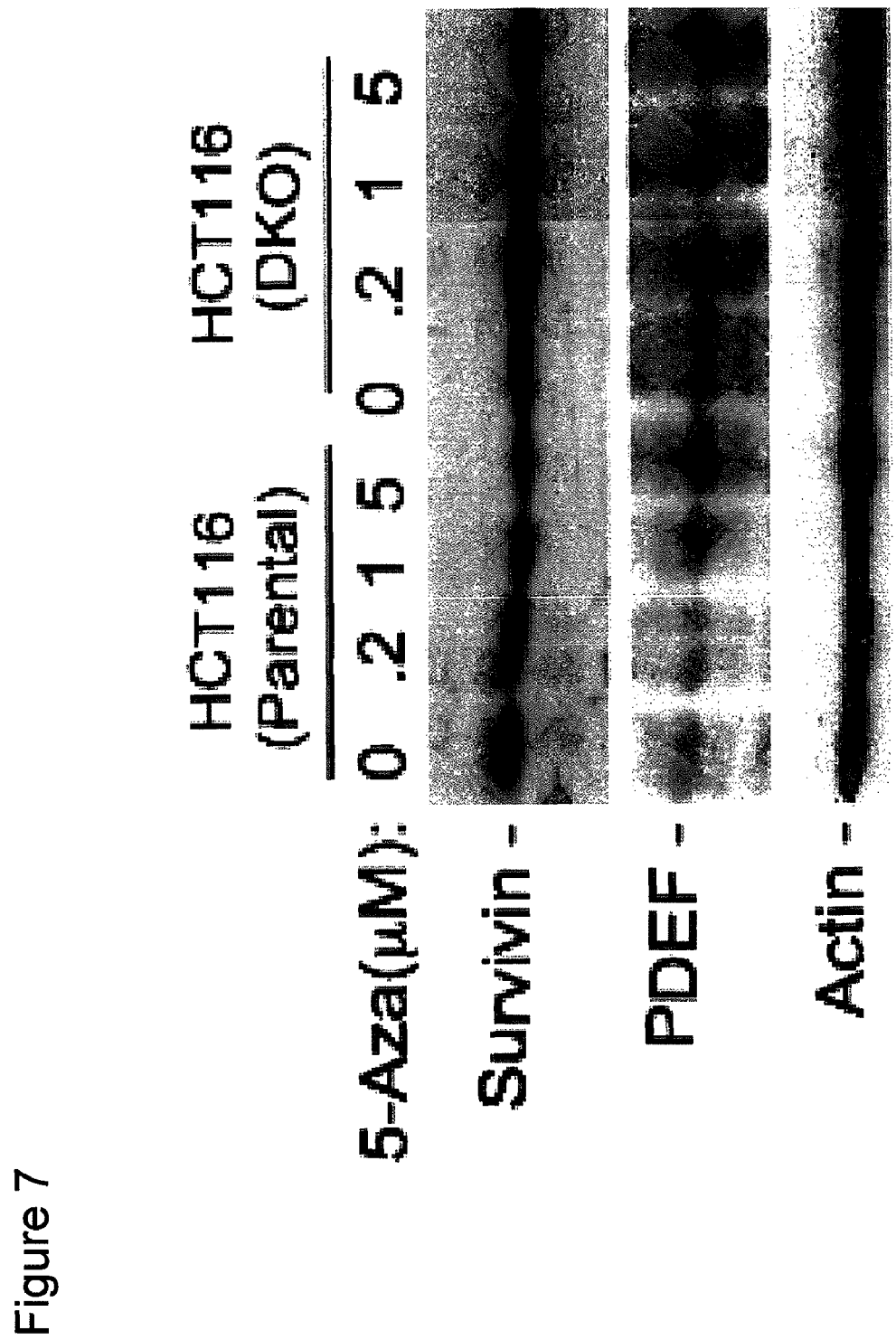
FIG. 7 provides a photographic representation of results obtained from differential modulation of survivin and PDEF expression in an HCT116 parental colon cancer cell line, versus in an HCT116 cell line in which both the DNMT1 and DNMT3b DNA methyltransferases have been knocked out. Both HCT116 parental and double knockout (DNMT1$^{-/-}$/DNMT3B$^{-/-}$) colon cancer cell lines were treated with and without the methylation inhibitor 5-Aza-dC for 3 days as shown. Cells were lysed and analyzed for the expression of survivin and PDEF by western blots. Actin is the internal control of protein loading.
Figure 8:
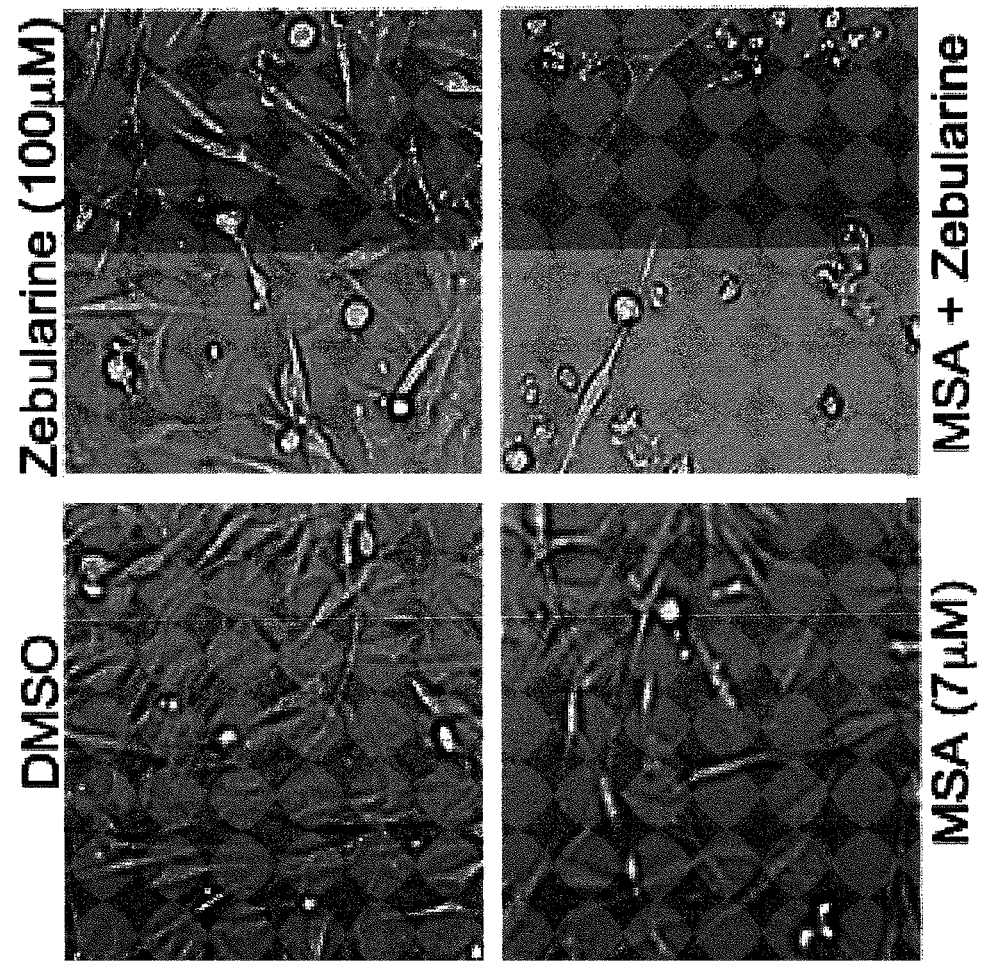
FIG. 8 provides a photographic representation of results showing a synergistic effect of DNA methylation inhibitors in combination with DNA methylation inducers/promoters on massive cancer cell death. Sequential treatment of MDA-MB-231 breast cancer cells with methylseleninic acid (MSA, a DNA methylation inducer/promoter) for 48 hours and Zebularine (a DNA methylation inhibitor) for 24 hours alone or in combination as shown. Growth medium with drugs was replaced with complete new medium without drugs 24 hour after Zebularine treatment. Images were then taken using a digital camera 48 hours after new medium replacement. Both MSA and Zebularine alone with the indicated concentration only moderately inhibit cell growth without induction of cell death. However, sequential combination of MSA and Zebularine (MSA 24 h and then Zebularine additional 24 h) induce massive cell death.

Consistent with the data shown in FIG. 6, as shown in FIG. 7, we demonstrate that 5-aza-2-deoxycytidine (5-Aza-dC) treatment of HCT116 parental colon cancer cells induces PDEF expression and decreases survivin expression. However, 5-Aza-dC showed no effect on survivin and PDEF expression in HCT116 colon cancer cells with double knock-out (DKO) of DNMT1 (DNA methaltransferase 1) and DNMT3b (DNA methaltransferase 3b). Since it is know that the survivin gene is not methylated, despite our identification of a CpG island in the survivin gene, this Example further supports that demethylation of PDEF via a DNA methylation inhibitor can facilitate downregulation of survivin expression.

EXAMPLE 5

This Example demonstrates the synergistic effects of DNA methylation inhibitors in combination with DNA methylation inducers/promoters on massive cancer cell death.

Sequential treatment of MDA-MB-231 breast cancer cells with methylseleninic acid (MSA, a DNA methylation inducer/promoter) for 48 hours and Zebularine (a DNA methylation inhibitor) for 24 hours alone or in combination as shown. Growth medium with drugs was replaced with complete new medium without drugs 24 hour after Zebularine treatment. Images were then taken using a digital camera 48 hours after new medium replacement. Both MSA and Zebularine alone with the indicated concentration only moderately inhibit cell growth without induction of cell death. However, sequential combination of MSA and Zebularine (MSA 24 h and then Zebularine additional 24 h) induce massive cell death.

Thus, as can be seen from the foregoing, we have demonstrated that PDEF protein is highly expressed in the epithelial cells of normal breast, prostate, ovarian and lung tissue. Our experiments have revealed that loss of PDEF expression during tumor initiation, progression and metastasis not only occurs in breast cancer but also in other types of cancers, including prostate, ovarian and lung cancers. Consistent with our finding that PDEF inhibits survivin expression and promoter activity in breast cancer, loss of PDEF expression is closely associated with the upregulation of survivin in other types of cancers as well, including ovarian, prostate and lung cancers tested. In the present invention we have discovered that, like the survivin gene, there is a CpG Island in the PDEF gene promoter/exon 1 junction region, as well as other regions of the PDEF gene, and that loss of PDEF expression and upregulation of survivin during tumor initiation, progression and metastasis is due to the hypermethylation of the PDEF gene CpG Island, while no DNA methylation was determined for the survivin gene. Furthermore, we have demonstrated that we are able to restore the expression of PDEF and downregulate survivin in cancer cells by using the methylation inhibitor, 5-Aza-dC. This has potential clinical importance because it provides a unique approach for determining which individuals could benefit from treatment of cancer through targeting PDEF and survivin as two interconnected targets via inhibition of DNA methylation of the PDEF gene.

We have also discovered that sequential treatment of MDA-MB-231 breast cancer cells with the DNA methylation inhibitor (Zebularine) and methylation promoter/inducer (MSA) synergistically induces massive cancer cell death. Our observation indicates that, while the methylation promoter agent induces survivin CpG motif methylation, it has no effect on PDEF demethylation by methylation inhibitors, which provides an explanation of the data showing synergistic effects on cell death shown in by the application of the methylation inhibitor and promoter in combination.

We claim:

1. A method for identifying whether or not an individual diagnosed with cancer is a candidate for receiving a DNA methylation inhibitor, the method comprising the steps of:
   a) obtaining a biological sample from cancerous tissue of the individual;
   b) determining PDEF expression and survivin expression from the sample;
   wherein the determining the PDEF expression is performed by analyzing the nucleotide sequence of a portion of the PDEF gene sufficient to permit detection of hypermethylation of said portion, wherein hypermethylation of said portion indicates that PDEF expression is absent or low relative to the matched PDEF expression control; and
   determining that the individual is a candidate for receiving the DNA methylation inhibitor by determining that PDEF expression is absent or low relative to a PDEF expression control and that survivin expression is present; or
   determining that the individual is a not candidate for receiving the DNA methylation inhibitor by determining that PDEF expression is normal or high relative to a PDEF expression control and survivin expression is absent; or determining that the individual is a not candidate for receiving the DNA methylation inhibitor by determining that PDEF expression is absent or low relative to a PDEF expression control and survivin expression is absent; or determining that the individual is a not candidate for receiving the DNA methylation inhibitor by determining that PDEF expression is normal or high relative to a PDEF expression control and survivin expression is present.

2. The method of claim 1, wherein the determining survivin expression is performed by determining survivin mRNA expression.

3. The method of claim 1, wherein the determining survivin expression is performed by determining survivin protein expression.

4. The method of claim 1, wherein the portion of the PDEF gene sufficient to permit detection of hypermethylation comprises SEQ ID NO:1.

5. The method of claim 1, wherein the individual is diagnosed with a cancer selected from the group of cancers consisting of breast cancer, prostate cancer, ovarian cancer and lung cancer.

6. The method of claim 1, wherein a determination that PDEF expression is absent or low relative to the PDEF expression control and that survivin expression is present is indicative that the individual is a candidate to receive a histone deacetylase inhibitor in combination with the DNA methylation inhibitor.

7. The method of claim 1, wherein a determination that PDEF expression is absent or low relative to the PDEF expression control and that survivin expression is present is indicative that the individual is a candidate to receive a DNA methylation promoter in addition to the DNA methylation inhibitor.

8. The method of claim 1, further comprising communicating identification of the individual as a candidate for receiving the DNA methylation inhibitor to a health care professional.

* * * * *

SEQUENCE LISTING

<160> NUMBER OF SEQ ID NOS: 11

<210> SEQ ID NO 1
<211> LENGTH: 201
<212> TYPE: DNA

<213> ORGANISM: Human

<400> SEQUENCE: 1

| gacacagccg ccagcccaaa cagcagcggc atgggcagcg ccagcccggg tctgagcagc | 60 |
| gtatccccca gccacctcct gctgcccccc gacacggtgt cgcggacagg cttggagaag | 120 |
| gcggcagcgg gggcagtggg tctcgagaga cgggactgga gtcccagtcc acccgccacg | 180 |
| cccgagcagg gcctgtccgc c | 201 |

<210> SEQ ID NO 2
<211> LENGTH: 210
<212> TYPE: DNA
<213> ORGANISM: Human

<400> SEQUENCE: 2

| gcgtgtccac ttccgctgcc acttgacatt cgctcatcac agtgctccac ccacaaggtc | 60 |
| agcagggcaa gcgttgttat cgccattcac agaggaggcg agggaggccc agagtgcttg | 120 |
| agactcgctc gtgatcccgc cgctcgtcag tggcagtgct gcacagaaac cgagatgtgg | 180 |
| gccctgagtt ccacccggtg ctctccacgc | 210 |

<210> SEQ ID NO 3
<211> LENGTH: 206
<212> TYPE: DNA
<213> ORGANISM: Human

<400> SEQUENCE: 3

| cgtttttgga ggccgaggca ggtggatagc ttgaggtcat gagctcaaga ccagcctggt | 60 |
| caacatggcg aaaccccgtc tctactaaaa atacaaaaat tagccgggcg tggtggtgcg | 120 |
| tgcctgtaat cccagctact cgagaggctg aggtaagaga tcacttgaa cccgggaggc | 180 |
| agaggtggca gtgagctgag actgcg | 206 |

<210> SEQ ID NO 4
<211> LENGTH: 198
<212> TYPE: DNA
<213> ORGANISM: Human

<400> SEQUENCE: 4

| cttgtctgtc tctggccctc agctgatcca tcttagaacc ccagccctgg acccactcga | 60 |
| cgtatctctg gcgccttgca cgtaatatga gctgagtggc tatgcagcaa ccaatgaacg | 120 |
| agtgaatgag cgagtgaatg aatgagtccc ctagctgtca gggcatggat ccccagcaa | 180 |
| ggaggggag acctgcaa | 198 |

<210> SEQ ID NO 5
<211> LENGTH: 170
<212> TYPE: DNA
<213> ORGANISM: Human

<400> SEQUENCE: 5

| cggctgtggg gcatccgcaa gaaccgtccc gccatgaact acgacaagct gagccgctcc | 60 |
| atccgccagt attacaagaa gggcatcatc cggaagccag acatctccca gcgcctcgtc | 120 |
| taccagttcg tgcacccat ctgagtgcct ggcccagggc ctgaaacccg | 170 |

<210> SEQ ID NO 6
<211> LENGTH: 20
<212> TYPE: DNA
<213> ORGANISM: Artificial Sequence
<220> FEATURE:

```
<223> OTHER INFORMATION: PCR primer

<400> SEQUENCE: 6
ttaggtagtt aatagatata                                                    20

<210> SEQ ID NO 7
<211> LENGTH: 22
<212> TYPE: DNA
<213> ORGANISM: Artificial sequence
<220> FEATURE:
<223> OTHER INFORMATION: PCR primer sequence

<400> SEQUENCE: 7
aataaactaa aactccaatc cc                                                 22

<210> SEQ ID NO 8
<211> LENGTH: 20
<212> TYPE: DNA
<213> ORGANISM: Artificial sequence
<220> FEATURE:
<223> OTHER INFORMATION: PCR primer

<400> SEQUENCE: 8
gtcgttagtt taaatagtag                                                    20

<210> SEQ ID NO 9
<211> LENGTH: 22
<212> TYPE: DNA
<213> ORGANISM: Artificial sequence
<220> FEATURE:
<223> OTHER INFORMATION: PCR primer

<400> SEQUENCE: 9
tggttaggtt ggttttgaat tt                                                 22

<210> SEQ ID NO 10
<211> LENGTH: 22
<212> TYPE: DNA
<213> ORGANISM: Artificial sequence
<220> FEATURE:
<223> OTHER INFORMATION: PCR primer

<400> SEQUENCE: 10
aaaacccaac cacaataacc tc                                                 22

<210> SEQ ID NO 11
<211> LENGTH: 26
<212> TYPE: DNA
<213> ORGANISM: Artificial Sequence
<220> FEATURE:
<223> OTHER INFORMATION: PCR primer

<400> SEQUENCE: 11
tggttttgaa ttttaggatt taagtg                                             26
```